(12) United States Patent
Huang et al.

(10) Patent No.: US 12,702,371 B2
(45) Date of Patent: Aug. 11, 2026

(54) HEAT DISSIPATION STRUCTURE AND INSPECTION APPARATUS

(71) Applicant: Nuctech Company Limited, Beijing (CN)

(72) Inventors: Qingping Huang, Beijing (CN); Mingzhi Hong, Beijing (CN); Zinan Wang, Beijing (CN); Liguo Zhang, Beijing (CN); Hongbin Hou, Beijing (CN)

(73) Assignee: Nuctech Company Limited, Beijing (CN)

( * ) Notice: Subject to any disclaimer, the term of this patent is extended or adjusted under 35 U.S.C. 154(b) by 136 days.

(21) Appl. No.: 18/718,509

(22) PCT Filed: Dec. 23, 2022

(86) PCT No.: PCT/CN2022/141437
§ 371 (c)(1),
(2) Date: Jun. 11, 2024

(87) PCT Pub. No.: WO2023/125292
PCT Pub. Date: Jul. 6, 2023

(65) Prior Publication Data

US 2025/0040900 A1 Feb. 6, 2025

(30) Foreign Application Priority Data

Dec. 31, 2021 (CN) ......................... 202111681959.2

(51) Int. Cl.
*A61B 6/00* (2006.01)
*F28D 1/03* (2006.01)
(Continued)

(52) U.S. Cl.
CPC .............. *A61B 6/4488* (2013.01); *F28D 1/03* (2013.01); *F28D 1/053* (2013.01); *H05G 1/025* (2013.01); *F28D 2021/0029* (2013.01)

(58) Field of Classification Search
CPC ......... A61B 6/4488; A61B 6/035; F28D 1/03; F28D 1/053; F28D 2021/0029;
(Continued)

(56) References Cited

U.S. PATENT DOCUMENTS 4,063,104 A * 12/1977 Gadd ....................... A61B 6/56 378/194
6,491,428 B1 12/2002 Takanashi
(Continued)

FOREIGN PATENT DOCUMENTS

CN 101219056 A 7/2008
CN 103732145 A 4/2014
(Continued)

OTHER PUBLICATIONS

"European Application No. 22217362.7, Communication dated May 8, 2023", (May 8, 2023), 8 pgs.
(Continued)

*Primary Examiner* — Kiho Kim
(74) *Attorney, Agent, or Firm* — Schwegman Lundberg & Woessner, P.A.

(57) ABSTRACT

A heat dissipation structure and an inspection apparatus are provided. The heat dissipation structure includes: a supporting frame configured to rotate around a central axis thereof; a heat source arranged on the supporting frame; and a radiator configured to receive a fluid heated by the heat source from the heat source and input the cooled fluid to the heat source. The radiator is arranged on a periphery of the supporting frame relative to the central axis. When the supporting frame rotates around the central axis, the radiator
(Continued)

allows air to enter into the radiator via an air inlet opening thereof and to be expelled from the radiator via an air outlet opening thereof.

14 Claims, 3 Drawing Sheets

(51) Int. Cl.

| | |
|---|---|
| ***F28D 1/053*** | (2006.01) |
| ***H05G 1/02*** | (2006.01) |
| *F28D 21/00* | (2006.01) |

(58) Field of Classification Search

CPC ...... H05G 1/025; G01V 5/226; G01T 1/2985; G01N 23/046

See application file for complete search history.

(56) References Cited

U.S. PATENT DOCUMENTS

| | | | |
|---|---|---|---|
| 9,251,994 | B2 | 2/2016 | Watanabe et al. |
| 9,351,694 | B2 | 5/2016 | Anno et al. |
| 2005/0089146 | A1 | 4/2005 | Toth et al. |
| 2006/0140345 | A1 | 6/2006 | Canfield et al. |
| 2014/0153689 | A1 | 6/2014 | Anno et al. |
| 2014/0314197 | A1 | 10/2014 | Watanabe et al. |
| 2017/0105692 | A1* | 4/2017 | Sawanobori ......... A61B 6/4488 |
| 2019/0000406 | A1 | 1/2019 | Liu et al. |

FOREIGN PATENT DOCUMENTS

| | | | |
|---|---|---|---|
| CN | 104113976 | A | 10/2014 |
| CN | 114324424 | A | 4/2022 |
| EP | 0030072 | A2 | 6/1981 |
| JP | H07194587 | A | 8/1995 |
| JP | 2001137224 | A | 5/2001 |
| JP | 2002345804 | A | 12/2002 |
| JP | 2006204399 | A | 8/2006 |
| JP | 2013056119 | A | 3/2013 |
| JP | 2019180927 | A | 10/2019 |
| JP | 2020028477 | A | 2/2020 |
| JP | 2021112464 | A | 8/2021 |
| JP | 2021142145 | A | 9/2021 |
| WO | WO-2023125292 | A1 | 7/2023 |

OTHER PUBLICATIONS

“International Application No. PCT/CN2022/141437, International Search Report and Written Opinion mailed Mar. 21, 2023”, (Mar. 21, 2023), 18 pgs.

“Japanese Application No. 2022-210467, Notice of Reasons for Refusal dated Sep. 19, 2023”, (Sep. 19, 2023), 12 pgs.

* cited by examiner

HEAT DISSIPATION STRUCTURE AND INSPECTION APPARATUS

PRIORITY CLAIM TO RELATED APPLICATIONS

This application is a U.S. national stage filing under 35 U.S.C. § 371 from International Application No. PCT/CN2022/141437, filed on 23 Dec. 2022, and published as WO2023/125292 on 6 Jul. 2023, which claims the benefit under 35 U.S.C. 119 to Chinese Application No. 202111681959.2, filed on 31 Dec. 2021, the benefit of priority of each of which is claimed herein, and which applications and publication are hereby incorporated herein by reference in their entirety.

TECHNICAL FIELD

The present disclosure relates to a field of security inspection, and in particular to a heat dissipation structure and an inspection apparatus.

BACKGROUND

The CT inspection apparatus is widely used in a variety of inspections, and has currently been used for security inspection of baggage articles. In the CT inspection apparatus, for example, an X-ray generator and a detection device are installed on a circular frame for rotary motion. A space limited by a central hole of the circular frame constitutes an inspection channel. Due to a large amount of heat generated when using a ray source, it is necessary to cool the ray source. The existing inspection apparatus is generally equipped with a fan to cool a radiator of the inspection apparatus, which makes the inspection apparatus complex in structure and frequent in failures. The fan may cause safety risks during use.

It is desirable to provide a CT inspection apparatus with improved performance to improve an inspection efficiency.

SUMMARY

According to an aspect of the present disclosure, a heat dissipation structure is provided, including: a supporting frame configured to rotate around a central axis of the supporting frame; a heat source arranged on the supporting frame and configured to rotate with the supporting frame; and a radiator configured to receive from the heat source a fluid heated by the heat source and input the cooled fluid to the heat source; the radiator is arranged on a periphery of the supporting frame relative to the central axis, and when the supporting frame rotates around the central axis of the supporting frame, the radiator is configured to allow air to enter into the radiator via an air inlet opening of the radiator and to be expelled from the radiator via an air outlet opening of the radiator.

In an embodiment, the radiator includes a first plate and a second plate, the first plate and the second plate are opposite each other to allow the air to pass between the first plate and the second plate so as to remove heat from the first plate and the second plate, and the first plate is farther away from the central axis than the second plate.

In an embodiment, the radiator includes a heat pipe arranged in the first plate and the second plate, and the fluid flows through the heat pipe.

In an embodiment, the radiator includes a plurality of heat sinks, and the plurality of heat sinks are connected between the first plate and the second plate and spaced apart from each other, so that two adjacent heat sinks between the first plate and the second plate define a channel allowing the air to flow.

In an embodiment, the plurality of heat sinks are arranged between the first plate and the second plate in parallel.

In an embodiment, the plurality of heat sinks are arranged to extend between the first plate and the second plate, and each of the plurality of heat sinks is at an angle with respect to a tangent direction of a circumferential trajectory of the plurality of heat sinks when the plurality of heat sinks rotate around the central axis.

In an embodiment, each of the plurality of heat sinks is arranged to extend meanderingly from the air inlet opening to the air outlet opening between the first plate and the second plate.

In an embodiment, each of the plurality of heat sinks is arranged to extend meanderingly in a radial direction relative to the central axis between the first plate and the second plate.

In an embodiment, the radiator further includes at least one connecting plate fixedly connected between the first plate and the second plate.

In an embodiment, the at least one connecting plate, the first plate and the second plate form a box structure, the box structure defining the air inlet opening, the air outlet opening and a gas path between the air inlet opening and the air outlet opening.

In an embodiment, an area of the first plate is not equal to an area of the second plate.

In an embodiment, the heat dissipation structure further includes a pump configured to pump the fluid out of the heat source and pump the fluid into the radiator, so that the fluid circulates between the heat source and the radiator.

In an embodiment, the heat dissipation structure further includes a container configured to be in fluid connection with the heat source, and the container is capable of storing the fluid pumped out of the heat source.

In an embodiment, the fluid is water or oil.

In an aspect of the present disclosure, an inspection apparatus is provided, including the heat dissipation structure described above, the heat source is a ray source arranged on the supporting frame to emit rays; the supporting frame is configured to define an inspection channel passing an axis of the supporting frame.

In an embodiment, the ray source is carried by the supporting frame to rotate around the inspection channel, and when the ray source rotates, the ray source is configured to emit rays toward an inspected object to acquire a three-dimensional image of the inspected object.

BRIEF DESCRIPTION OF THE DRAWINGS

One or more embodiments of the present disclosure will now be described, by way of example only, with reference to the accompanying drawings.

DETAILED DESCRIPTION OF EMBODIMENTS

In the following embodiments, terms “first”, “second”, and the like are used to distinguish different components, rather than sequencing or indicating primary or secondary. Terms “upper”, “lower”, and the like indicating orientations in the specification do not indicate an absolute orientation, but indicate a relative position between components.

Figures 1, 2:
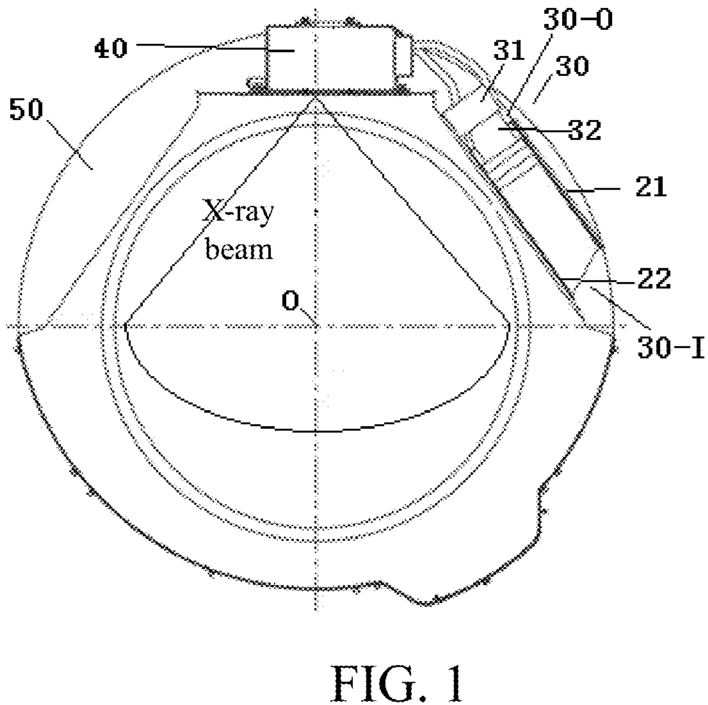
FIG. 1 shows a schematic top view of an inspection apparatus according to an embodiment of the present disclosure.
FIG. 2 shows a schematic perspective view of a heat dissipation structure according to an embodiment of the present disclosure.

As shown in FIG. 1, the embodiments of the present disclosure provide a heat dissipation structure including a supporting frame 50, and the supporting frame is used to rotate around a central axis O of the supporting frame. The supporting frame 50 shown in FIG. 1 is generally cylindrical in shape, defining a circular channel penetrating the supporting frame 50. The supporting frame 50 may carry a measuring tool or a processing tool, as well as devices such as a radiator 30, a motor and the like. The supporting frame 50 is rotatable for operation of the tool carried thereon. In an embodiment, the supporting frame 50 is a ring. In another embodiment, the supporting frame 50 may be a frame having another shape.

In an embodiment, the heat dissipation structure includes a heat source 40 arranged on the supporting frame 50 and rotating with the supporting frame 50. The heat source 40 may be the measuring tool or the processing tool. For example, the heat source 40 may be a ray source. The ray source may emit a ray which may generate a large amount of heat during operation, and thus a heat dissipation is required. The heat source 40 may be a heat source 40 of another type, which is mounted on a part of the supporting frame 50.

In an embodiment, the heat dissipation structure includes a radiator 30 configured to receive a fluid heated by the heat source 40 from the heat source 40 and input the cooled fluid to the heat source 40. Using the radiator 30 for the fluid is advantageous, which allows the fluid to circulate between the heat source and the radiator 30 so as to transfer the heat generated by the heat source to the radiator 30. At the same time, the radiator 30 may be separated from the heat source 40, so that an arrangement of the apparatus is more flexible. The circulation of the fluid may be realized through a heat pipe, which is included inside the heat source 40 and the radiator 30, and the fluid flows in the heat pipe. Optionally, the circulation may be achieved by a pump 31 driving the fluid to flow inside the heat pipe inside the heat source and the radiator 30. The heat pipe may be a metal pipe, a ceramic pipe or a pipe formed by other heat conductive materials. In the embodiment shown in FIG. 1, the pump 31 is arranged to allow the fluid in the heat pipe to pass through the pump 31, and the pump 31 drives the fluid to flow. Specifically, the pump 31 is configured to pump the fluid out of the heat source 40 and pump the fluid into the radiator 30 so that the fluid circulates between the heat source 40 and the radiator 30. In an embodiment, the heat dissipation structure further includes a container configured to be in fluid connection with the heat source 40 and capable of storing the fluid pumped from the heat source 40. The fluid in the container flows into the radiator for cooling under an action of the pump. For example, under the action of the pump 31, the fluid heated by the heat source first flows into a container such as a water tank 32 and then flows into the radiator 30, the fluid flows back to the heat source after cooling. In an embodiment, the pump 31 may be fixed on the water tank 32, so that a structure is more compact. The water tank 32 may make the fluid flow more uniformly in the heat pipe, and an impact brought by the pump may be buffered. In other embodiments, the pump 31 may be located in another location or may be arranged separately from the water tank 32. In other embodiments, the container may be a glass container or the like. In an embodiment, the fluid used for heat dissipation is water, aqueous solution, oil or other liquids.

Figure 3:
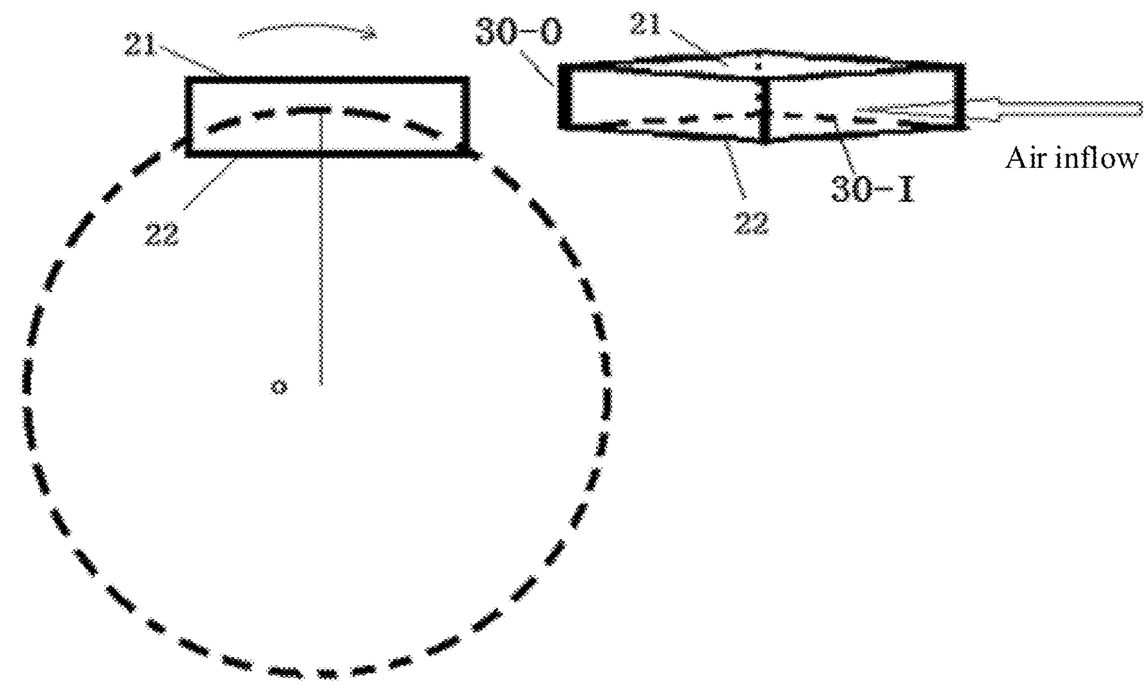
FIG. 3 shows a schematic view of a movement of a heat dissipation structure according to an embodiment of the present disclosure, wherein a schematic diagram at an upper right portion shows a schematic diagram of air entering a radiator.

In an embodiment, the radiator 30 is arranged on a periphery of the supporting frame 50 relative to the central axis O, and the radiator 30 allows air to enter into the radiator 30 via an air inlet opening 30-I of the radiator 30 and allows the air to be expelled from the radiator 30 via an air outlet opening 30-O of the radiator 30 when the supporting frame 50 rotates around the central axis O of the supporting frame 50. FIG. 3 shows a schematic diagram of the radiator 30 moving in a circle with the supporting frame 50. As shown in FIG. 3, it is advantageous for the radiator 30 to be arranged on the periphery of the supporting frame 50 relative to the central axis O. In this way, when the supporting frame 50 rotates, the radiator 30 has a maximum linear velocity, and a relative linear velocity of air entering the air inlet opening 30-I (that is, the linear velocity relative to the radiator 30) may be relatively large, thus allowing the air to take the heat of the radiator 30 away. It should be understood here that the supporting frame 50 is not necessarily circular. Even if the supporting frame 50 is provided as another shape due to functional requirements, the “periphery” of the supporting frame 50 may indicate that a position of the radiator 30 allows the radiator 30 to have a greater linear velocity than other parts of the supporting frame 50 when the supporting frame 50 rotates. In an embodiment, the supporting frame 50 may have a ring shape, or the supporting frame 50 may have a cylinder shape or the like.

As shown in FIG. 1 to FIG. 3, the radiator 30 may have a shape of a cuboid. One end of the radiator 30 is the air inlet opening 30-I, and the other end of the radiator 30 is the air outlet opening 30-O. The air passes through a path between the air inlet opening 30-I and the air outlet opening 30-O to taking away the heat of the radiator 30 to achieve a purpose of cooling. The radiator 30 may have other shapes. The radiator 30 may be composed of a first plate 21 and a second plate 22 via a connecting plate. For example, there may be two connecting plates, so that the first plate 21, the second plate 22 and the two connecting plates together form a box structure, or a structure defining an internal channel. It should be understood that the first plate 21, the second plate 22 and the connecting plate may form a variety of forms. The connecting plate, the first plate 21 and the second plate 22 form the box structure, defining the air inlet opening 30-I, the air outlet opening 30-O and a gas path between the air inlet opening 30-I and the air outlet opening 30-O.

In the embodiment shown in FIG. 2, an area of the first plate 21 is not equal to an area of the second plate 22. Such arrangement may make the shape of the radiator 30 conform to the shape of the supporting frame 50, and the first plate 21 will not protrude outside the periphery of the supporting frame 50, making an overall structure of the supporting frame 50 compact. It should be known that this is not necessary. The first plate 21 and the second plate 22 may have equal area or shape, and the area of the first plate 21 may even be larger than the area of the second plate 22, so that a flow of air entering the radiator 30 is further improved.

In an embodiment, the radiator 30 includes the first plate 21 and the second plate 22 arranged opposite each other, and the air is allowed to pass between the first plate 21 and the second plate 22 so as to transfer the heat on the first plate 21 and the second plate 22. On the supporting frame 50, the first plate 21 is farther away from the central axis O than the second plate 22, or the first plate 21 is located on an outer side of the supporting frame 50 away from the center, and the second plate 22 is located on an inner side of the supporting frame 50 close to the center. The first plate 21 and the second plate 22 may be parallel, however, this is not necessary.

In an embodiment, the radiator 30 includes the heat pipe arranged in the first plate 21 and the second plate 22, and the fluid flows through the heat pipe. The heat pipe transfers the heat of the liquid flowing therein to the first plate 21 and the second plate 22. The heat pipe may be distributed in at least one of the first plate 21 and the second plate 22, for example, extending meanderingly in at least one of the first plate 21 and the second plate 22, so that the heat pipe as long as possible may extend in the first plate 21 and/or the second plate 22 to achieve more sufficient heat transfer.

FIG. 2 shows a part of the heat pipe. As shown in FIG. 2, the fluid may enter the first plate 21 from a heat pipe inlet 11 of the first plate 21, and enter the second plate 22 through a heat pipe portion 13 connected between the first plate 21 and the second plate 22. After circulating in the second plate 22, the fluid may be discharged from the second plate 22 through a heat pipe outlet 12, and then the cooled fluid may enter the heat source.

In an embodiment, the first plate 21, the second plate 22 and the heat pipe may be formed of a metal pipe, a ceramic pipe or pipes of other materials. The heat pipe in the first plate 21 and the second plate 22 may be omitted. For example, a pipeline may be formed inside the first plate 21 and the second plate 22. It is only required for the heat pipe to connect the first plate 21 and the second plate 22 outside the first plate 21 and the second plate 22, thus allowing the liquid to flow from the heat source 40 into the first plate 21 and the second plate 22 through the heat pipe. The first plate 21 and the second plate 22 are connected by the heat pipe.

Figure 4:
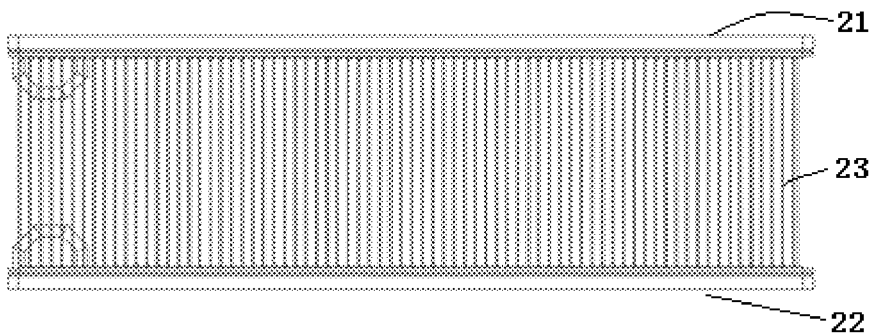
FIG. 4 shows a schematic diagram of a radiator according to an embodiment of the present disclosure.
Figure 5:
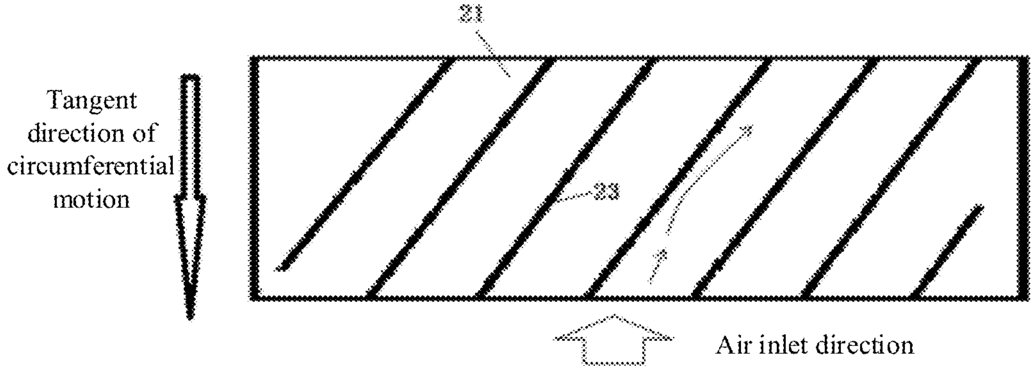
FIG. 5 shows a schematic diagram of a radiator according to an embodiment of the present disclosure.
Figure 6:
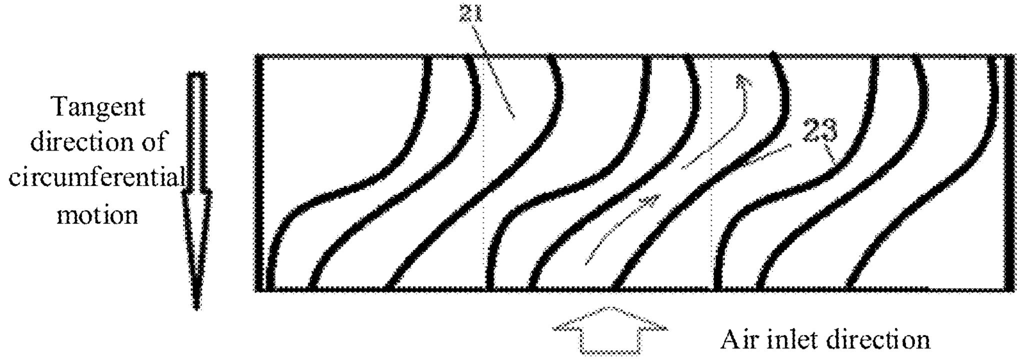
FIG. 6 shows a schematic diagram of a radiator according to an embodiment of the present disclosure.

In an embodiment, as shown in FIG. 4 to FIG. 6, the radiator 30 includes a plurality of heat sinks 23. The plurality of heat sinks are connected between the first plate 21 and the second plate 22, and are spaced apart from each other, so that two adjacent heat sinks 23 between the first plate 21 and the second plate 22 define a channel that allows air to flow. The heat sink 23 may be connected to the first plate 21 and the second plate 22 by, for example, welding. The heat sink 23 may be a metal sheet such as aluminum, copper, steel, or a sheet or plate formed by other heat conductive materials such as a ceramic sheet. Two ends of the heat sink 23 are respectively connected to the first plate 21 and the second plate 22. The heat sinks 23 are spaced apart from each other, so that a small channel having openings at two ends is formed between the first plate 21, the second plate 22 and the adjacent heat sinks 23. The plurality of heat sinks 23 between the first plate 21 and the second plate 22 form a plurality of small channels between the first plate 21 and the second plate 22. The small channel here is relative to the channel of the radiator 30, that is, the channel between the air inlet opening 30-I and the air outlet opening 30-O and between the first plate 21 and the second plate 22 of the radiator 30 are constituted by the plurality of small channels among the heat sinks 23. Hereinafter, the small channel is referred to as a sub channel. It should be understood that the channel and the sub channel have an inclusion relationship. The channel has a guiding effect on the air, and the sub channel also has a guiding effect on the air.

In an embodiment, as shown in FIG. 4, the plurality of heat sinks 23 are arranged between the first plate 21 and the second plate 22 in parallel. However, this is not necessary. The plurality of heat sinks 23 being arranged in parallel with each other may make a manufacturing process simple, and the heat on the heat sinks 23 may be taken away when the air passes through a gap between the heat sinks 23, thus realizing the cooling of the radiator 30. In the embodiment, since the radiator 30 rotates with the supporting frame 50, and the radiator 30 has a linear velocity relative to the air, there is no need to provide a cooling fan, and the radiator 30 may also effectively exchange the heat with the air, achieving a simple structure and good cooling effect.

In an embodiment, the plurality of heat sinks 23 are arranged to extend between the first plate 21 and the second plate 22, and each of the plurality of heat sinks 23 is at an angle with respect to a tangent direction of a circumferential trajectory when the plurality of heat sinks 23 rotate around the central axis O. As shown in FIG. 5, FIG. 5 is a top view of the radiator 30 (viewed from the first plate 21 toward the second plate 22). The tangent direction of the circumferential trajectory may be seen to be close to an air inlet direction shown in FIG. 5, while an extension direction of the heat sink 23 is inclined relative to the air inlet direction. Since the heat sink 23 is at an angle relative to the air inlet direction, the air entering the radiator 30 is blocked by the heat sink 23 and flows along a surface of the heat sink 23, and a certain pressure is generated between the heat sink 23 and the air, thereby increasing a heat exchange effect between the heat sink 23 and the air. Furthermore, since a length of the heat sink 23 increases after being inclined, a contact area of the heat sink with the air increases. The heat sink 23 shown in FIG. 5 inclines toward right, and it should be known that the heat sink 23 may incline toward left. In another embodiment, the heat sinks 23 may not be parallel to each other. In a rotating process of the radiator 30 in FIG. 5, an inclined arrangement of the heat sink 23 produces a whirlwind effect, greatly improving the heat dissipation effect.

In an embodiment, as shown in FIG. 6, FIG. 6 shows a top view of the radiator 30 (viewed from the first plate 21 toward the second plate 22). In the radiator 30 shown in FIG. 6, each of the plurality of heat sinks 23 is arranged to extend meanderingly from the air inlet opening 30-I toward the air outlet opening 30-O between the first plate 21 and the second plate 22, or each of the plurality of heat sinks 23 is arranged to extend meanderingly on a circumferential trajectory when plurality of heat sinks 23 rotate around the central axis O. Different from the arrangement of the heat sink 23 in FIG. 4, since the heat sink 23 is not arranged parallel to the air inlet direction, a transmission direction of the air is changed by the heat sink 23 after the air entering the radiator 30, so that a force is generated between the air and the heat sink 23, the air forms a turbulence flow in the sub channel between the heat sinks 23, thus a heat exchange between the air and the heat sink 23 is strengthened, and the heat dissipation effect of the radiator 30 is improved. It should be understood that the heat sink 23 may have other meandering forms. Here, the meandering represents a non-linear shape of the heat sink 23.

In an embodiment, the plurality of heat sinks 23 may extend meanderingly from an air inlet to an exhaust outlet, and each of the plurality of heat sinks 23 may be arranged to extend meanderingly from the first plate 21 to the second plate 22 in a radial direction relative to the central axis O. In the embodiment, the air forms the turbulence flow in the sub channel between the heat sinks 23, thereby further improving the heat transfer effect between the air and the heat sink.

An aspect of the present disclosure provides an inspection apparatus including the above-mentioned heat dissipation structure. In the embodiment, the heat source 40 is a ray source arranged on the supporting frame 50 to emit a ray. The supporting frame 50 defines an inspection channel passing the central axis of the supporting frame. In practical applications, an inspected object passes through the inspection channel defined by the supporting frame 50, and ray source emits rays as shown in FIG. 1. Structure and composition information of the object may be obtained by detecting the rays penetrating the inspected object. The inspection apparatus may further include a detector.

During inspection, the inspection apparatus may control the supporting frame 50 to rotate at a predetermined speed while the ray source emits rays, thereby being capable of emitting rays toward the object at a plurality of angles, ray signals penetrating the object is collected and a three-dimensional image of the object is reconstructed by a computer. The inspection apparatus may be a CT inspection apparatus.

Without departing from the scope of the appended claims, those of ordinary skill in the art may conceive other assemblies, devices and features thereof. In particular, it should be noted that, as will be understood by those skilled in the art, one or more features included in one or more drawings may be integrated into the device shown in another drawing. It should be understood that the detailed descriptions and specific examples are only given by way of illustration, and various changes and modifications within the spirit and the scope of the present disclosure will become apparent to those skilled in the art through the descriptions.

What is claimed is:

1. A heat dissipation structure, comprising:

a supporting frame configured to rotate around a central axis of the supporting frame;

a heat source arranged on the supporting frame and configured to rotate with the supporting frame; and a radiator configured to receive from the heat source a fluid heated by the heat source and input the cooled fluid to the heat source;

wherein the radiator is arranged on a periphery of the supporting frame relative to the central axis, and when the supporting frame rotates around the central axis of the supporting frame, the radiator is configured to allow air to enter into the radiator via an air inlet opening of the radiator and to be expelled from the radiator via an air outlet opening of the radiator;

wherein the radiator comprises a first plate and a second plate, the first plate and the second plate are opposite each other to allow the air to pass between the first plate and the second plate so as to remove heat from the first plate and the second plate, and the first plate is farther away from the central axis than the second plate; and wherein the radiator comprises a heat pipe arranged in the first plate and the second plate, and the fluid flows through the heat pipe.

2. The heat dissipation structure according to claim 1, wherein the radiator comprises a plurality of heat sinks, and the plurality of heat sinks are connected between the first plate and the second plate and spaced apart from each other, so that two adjacent heat sinks between the first plate and the second plate define a channel allowing the air to flow.

3. The heat dissipation structure according to claim 2, wherein the plurality of heat sinks are arranged between the first plate and the second plate in parallel.

4. The heat dissipation structure according to claim 2, wherein the plurality of heat sinks are arranged to extend between the first plate and the second plate, and each of the plurality of heat sinks is at an angle with respect to a tangent direction of a circumferential trajectory of the plurality of heat sinks when the plurality of heat sinks rotate around the central axis.

5. The heat dissipation structure according to claim 2, wherein each of the plurality of heat sinks is arranged to extend meanderingly from the air inlet opening to the air outlet opening and between the first plate and the second plate.

6. The heat dissipation structure according to claim 2, wherein each of the plurality of heat sinks is arranged to extend meanderingly in a radial direction relative to the central axis between the first plate and the second plate.

7. The heat dissipation structure according to claim 1, wherein the radiator further comprises at least one connecting plate fixedly connected between the first plate and the second plate.

8. The heat dissipation structure according to claim 7, wherein the at least one connecting plate, the first plate and the second plate form a box structure, the box structure defining the air inlet opening, the air outlet opening and a gas path between the air inlet opening and the air outlet opening.

9. The heat dissipation structure according to claim 1, wherein an area of the first plate is not equal to an area of the second plate.

10. The heat dissipation structure according to claim 1, further comprising a pump configured to pump the fluid out of the heat source and pump the fluid into the radiator, so that the fluid circulates between the heat source and the radiator.

11. The heat dissipation structure according to claim 1, further comprising a container configured to be in fluid connection with the heat source, and the container is capable of storing the fluid pumped out of the heat source.

12. The heat dissipation structure according to claim 1, wherein the fluid is water or oil.

13. An inspection apparatus, comprising the heat dissipation structure according to claim 1, wherein the heat source is a ray source arranged on the supporting frame to emit rays;

wherein the supporting frame is configured to define an inspection channel passing the central axis of the supporting frame.

14. The inspection apparatus according to claim 13, wherein the ray source is carried by the supporting frame to rotate around the inspection channel, and when the ray source rotates, the ray source is configured to emit rays toward an inspected object to acquire a three-dimensional image of the inspected object.

* * * * *